United States Patent [19]

Favre et al.

[11] Patent Number: 5,324,821

[45] Date of Patent: Jun. 28, 1994

[54] METHOD OF PREPARING A LIPOPROTEIN MODIFIED BY INCORPORATION OF A LIPOPHILIC ACTIVE SUBSTANCE

[75] Inventors: Gilles Favre, Toulouse; Patrick Duriez; Francoise Monard, both of Lille; Samadi-Baboli Medhi, Venerque; Georges Soula, Toulouse; Jean-Charles Fruchart, Ennetieres En Weppes, all of France

[73] Assignees: Universite Droit et Sante Lille II, Lille; Universite Paul Sabatier Toulouse III, Toulouse, both of France

[21] Appl. No.: 838,444

[22] PCT Filed: Jul. 12, 1991

[86] PCT No.: PCT/FR91/00573

§ 371 Date: May 6, 1992

§ 102(e) Date: May 6, 1992

[87] PCT Pub. No.: WO92/00761

PCT Pub. Date: Jan. 23, 1992

[30] Foreign Application Priority Data

Jul. 13, 1990 [FR] France .............................. 90 08980

[51] Int. Cl.$^5$ .......................... C07K 3/08; C07K 15/16
[52] U.S. Cl. ...................................... 530/359; 436/71; 424/450; 530/402
[58] Field of Search .................. 514/78, 75, 767, 773, 514/937, 943, 786, 2, 12, 21; 424/450; 436/71; 530/402, 403, 406, 410, 359

[56] References Cited

U.S. PATENT DOCUMENTS

| | | | |
|---|---|---|---|
| 5,023,271 | 6/1991 | Vigne et al. | 514/458 |
| 5,084,441 | 1/1992 | Shaw et al. | 514/2 |
| 5,169,933 | 12/1992 | Anderson et al. | 530/308 |

FOREIGN PATENT DOCUMENTS

| | | |
|---|---|---|
| 0277849 | 8/1988 | European Pat. Off. . |
| 2631236 | 11/1989 | France . |
| 0163824 | 2/1984 | Japan . |
| 86/07540 | 12/1986 | PCT Int'l Appl. . |
| 87/01035 | 2/1987 | PCT Int'l Appl. . |
| 88/09345 | 12/1988 | PCT Int'l Appl. . |

OTHER PUBLICATIONS

Samadi-Baboli, et al., Eur. J. Cancer Clin. Oneal. 25, 233–241 (1989).
The Merck Index, 11th Edition, S. Budavari, ed. Merck and Co., Rahway, NJ (1989), p. 555.
Counsell et al., "Lipoproteins as Potential Site-Specific Delivery Systems for Diagnostic and Therapeutic Agents", Journal of Medicinal Chemistry, vol. 25, No. 10, 100/82, American Chemical Society, pp. 1115–1120.
Chemical Abstract No. 127579a, Chemical Abstracts, vol. 102, No. 15 (1985).
Chemical Abstract No. 197780k, Chemical Abstracts, vol. 113, No. 22 (1990).
Brown et al., "A Receptor-Medicated Pathway for Cholesterol Homeostasis", *Science, vol. 232, pp. 34–47, Apr. 1986.*
Basu et al., "Degradation of Cationized Low Density Lipoprotein and Regulation of Cholesterol Metabolism in Homozygous Familial Hypercholesterolemia Fibroblasts", *Proc. Matl. Acad. Sci. USA*, vol. 73, No. 9, pp. 3178–3182, Sep. 1976.

(List continued on next page.)

Primary Examiner—Michael G. Wityshyn
Assistant Examiner—C. Sayala
Attorney, Agent, or Firm—Oliff & Berridge

[57] ABSTRACT

Method of preparing a lipoprotein modified by incorporation of at least one lipophilic active substance other than a triglyceride, characterized by incorporation of said active substance into an emulsion of a lipid phase in a continuous aqueous phase, by adding to the emulsion, with stirring, an original lipoprotein and at least one lipid transfer protein, allowing the mixture to incubate, and, using known methods, isolating the lipoprotein into which the active substance is incorporated; a lipoprotein thus obtained, and pharmaceutical or cosmetic composition containing such a modified lipoprotein.

24 Claims, No Drawings

OTHER PUBLICATIONS

Jarnagin et al., "Isolation and Specificity of a $M_r$ 74,000 Cholesteryl Ester Transfer Protein from Human Plasma", *Proc. Natl. Acad. Sci. USA*, vol. 84, pp. 1854–1857, Apr. 1987.

Granot et al., "Core Modification of Human Low-Density Lipoprotein by Artificial Triacylglycerol Emulsion", *Biochimica et Biophyscia Acta*, vol. 833, pp. 308–315, 1985.

Yokoyama et al., "Plasmapheresis Therapy of Hypercholesterolemias", *Plasmapheresis*, pp. 231–237, 1983.

Shaw et al., "Induction of Macrophage Antitumor Activity by Acetylated Low Density Liproprotein Containing Lipophilic Muramyl Tripeptide Density Lipoprotein Containing Lipophilic Muramyl Tripeptide", *Proc. Natl. Acad. Sci. USA*, vol. 85, pp. 6112–6116, Aug. 1988.

Steinbrecher, "Oxidation of Human Low Density Lipoprotein Results in Derivatization of Lysine Residues of Apolipoprotein B by Lipid Peroxide Decomposition Products", *The Journal of Biological Chemistry*, vol. 262, No. 8, pp. 3603–3608, Mar. 15, 1987.

Grosbis et al., "Changes in Level and Activity of Phospholipid Transfer Protein During Maturation and Germination of Maize Seeds", *Plant Physiol.*, vol. 90, pp. 1560–1564, 1989.

Bastiras et al., "Purification of Human Plasma Lipid Transfer Protein Using Fast Protein Liquid Chromatography", *Journal of Chromatography*, vol. 383, pp. 27–34, 1986.

Bijsterbosch et al., "Lactosylated Low Density Lipoprotein: A Potential Carrier for the Site-Specific Delivery of Drugs to Kupffer Cells", *Molecular Pharmacology*, vol. 36, pp. 484–486.

Kato et al., "Purification, Microheterogeneity, and Stability of Human Lipid Transfer Protein", *The Journal of Biological Chemistry*, vol. 264, No. 7, pp. 4082–4087, 1989.

Yokoyama et al., "Selective Removal of Low Density Lipoprotein by Plasmapheresis in Familial Hypercholesterolemia," *Arteriosclerosis*, vol. 5, No. 6, pp. 613–622, Nov./Dec. 1985.

METHOD OF PREPARING A LIPOPROTEIN MODIFIED BY INCORPORATION OF A LIPOPHILIC ACTIVE SUBSTANCE

FIELD OF THE INVENTION

The present invention relates to a method of preparing a lipoprotein modified by incorporation of a lipophilic active substance as well as a pharmaceutical or cosmetic composition containing a lipoprotein modified in this way as an active ingredient.

BACKGROUND OF THE INVENTION

It is known that one of the current objectives of pharmaceutical research is to direct drugs to the target organs and/or cells in order to enhance therapeutic efficacy while reducing side effects. One of the means of achieving this objective consists of binding the drug to a molecule, a macromolecule for example, able to play the role of carrier (or "vector") of the drug and bring it specifically to the target organ or target cells.

A number of macromolecules or molecule combinations such as liposomes, nanocapsules, DNA, lectins, antibodies, and lipoproteins have already been used or proposed as biologically active carrier substances.

It is known that lipoproteins constitute an important group of serum proteins comprising a lipid core surrounded by an envelope containing in particular phospholipids and specific proteins (apolipoproteins).

Lipoproteins are the systems that store and carry lipids, particularly cholesterol.

It is known that lipoproteins are classified by density. A distinction is made between:

- chylomicrons which are particles with densities less than 0.96;
- very-low-density lipoproteins (VLDL) with densities between 0.96 and 1.006 g/cm$^3$
- low-density lipoproteins (LDL) with densities between approximately 1.019 and 1.063;
- high-density lipoproteins (HDL) with densities between approximately 1.063 and 1.21.

Lipoproteins have marked tropism for various cells that have apolipoprotein receptors; in addition, in certain cases, they may be captured by cells in the reticuloendothelial system (phagocytic cells).

Hence it can be seen that lipoproteins are capable of being useful drug carriers. It has already been proposed to use lipoproteins, LDLs in particular, as drug vectors (see, for example, International Patent Application PCT No. WO 86/07540 and European Patent Application No. 0277849).

The low-density lipoproteins (LDLs), which have been the most studied as drug vectors, are spherical particles with diameters of approximately 20 nm. Each particle has a core composed of about 1500 cholesterol ester molecules and an envelope composed of cholesterol, phospholipids, and apolipoproteins (apolipoprotein B or apo B).

Mammal cells have receptors that recognize apo B and bind the LDLs to their surfaces. After binding to the membrane surface of the cells, the LDLs are internalized by endocytosis and carried to the lysosomes where they are broken down to meet the needs of the cell, particularly its cholesterol needs.

If native LDLs, i.e. LDLs that are not chemically modified, are used, the LDL-drug complex behaves like the native LDLs, namely it remains in the bloodstream for two to three days and is recognized by cells that have the apo B receptor (S. M. Brown and J. L. Goldstein, Science, 232, 34-47, 1986). This is the case for cancer cells which have a high level of apo B receptor.

It is also known that chemically modified lipoproteins (acetylates, acetoacetylates, oxide compounds, lactosylates, etc.) are recognized and captured by cells in the reticuloendothelial system, particularly by macrophages. Here again, the (chemically modified) lipoprotein-drug complex behaves in the organism like the original modified lipoprotein and is captured by macrophages through the intermediary of the acetylated LDL receptor (scavenger receptor) (see, for example, J. M. Shaw et al., Proc. Natl. Acad. Sci. USA Vol. 85, pp. 6112-6116 (1988) and M. K. Bijsterbock et al., Molecular Pharmacology, 36, pp. 484-486 (1989)).

In the organism, the transfer of triglycerides and of cholesterol esters and phospholipid between the various classes of lipoproteins (LDLs, VLDLs, HDLs, and chylomicrons) is carried out by proteins known as transfer proteins which have a higher density than lipoproteins, and which are accordingly contained in the residue of ultracentrifuged human or animal plasma after separation of the lipoproteins. Such a centrifugation residue constitutes the fraction known as LPDS (lipoproteindeficient serum), which has in particular the properties of the transfer protein it contains. Some of these transfer proteins have already been isolated and described (see, for example, A. S. Jarnagin et al., Proc. Natl. Acad. Sci. U.S.A. Vol. 84, pp. 1854-57 (1987); Kato et al., J. Biol. Chem. (US), 264, No. 7, 4082-4087 (1989); and Bastiras and Calvert, J. Chromatogr. Biomed. Appl. 383, No. 1, pp. 27-34 (1986)).

Transfer proteins are capable of providing, for example, transport of triglycerides from the VLDLs to the LDLs. They are also capable of transporting triglycerides from artificial triglyceride emulsions to LDLs (see, for example, E. Granot et al., Biochimica et Biophysica Acta 833, pp. 308-315 (1985)).

It has now been discovered that the proteins contained in LPDS are also capable of transporting lipophilic biologically active substances in vitro, other than triglycerides and cholesterol esters, particularly non-physiologic drugs, from lipid emulsions containing such lipophilic substances to lipoproteins, with these substances being incorporated into the lipoproteins.

This process of incorporation of biologically active substances into lipoproteins is useful because it avoids the use of undesirable substances such as detergents, and thanks to the use of natural transfer agents, it avoids any alteration of LDL biological activity.

SUMMARY OF THE INVENTION

Hence, an object of the present invention is to provide to provide a method of preparing a lipoprotein modified by incorporation of at least one lipophilic active substance other than a triglyceride or a cholesterol ester, characterized by incorporation of said active substance into an emulsion of a lipid phase in a continuous aqueous phase, by adding to the emulsion, with stirring, an original lipoprotein and at least one lipid transfer protein, allowing the mixture to incubate, and, using known methods, isolating the lipoprotein into which the active substance is incorporated.

The lipophilic active substance which is to be incorporated into the lipoprotein is different from the components of the lipid phase of the emulsion. However, the above definition of the method according to the invention does not mean that lipophilic substances such as triglycerides or cholesterol esters that may be present in the lipid phase will not be incorporated into the lipoproteins at the same time as said active substance. In fact a certain proportion of these lipophilic substances present in the lipid phase is generally incorporated into the lipoproteins at the same time as the active substance.

DETAILED DESCRIPTION OF THE PREFERRED EMBODIMENTS

The method according to the invention may also have the characteristics to be described below, taken separately or in combination.

The lipophilic active substance which may be incorporated into the lipoproteins by means of the method according to the invention may be chosen in particular among antineoplastic, immunostimulant, immunosuppressant, antiviral, antibacterial, antifungal, antiparasitic, etc. drugs or fat-soluble cosmetic active substances. If the drug is not sufficiently lipophilic to be incorporated spontaneously into the lipid phase of the emulsion, it may be modified chemically to be made lipophilic (or more lipophilic) by grafting, according to known methods, a lipophilic group such as, for example, the acyl residue of a fatty acid having at least eight carbon atoms, or a steroid group derived for example from cholane or cholestane and having a reactive function allowing it to be grafted to the active substance to be incorporated.

The lipid phase of the emulsion may be any appropriate lipid emulsion. For example, the lipid phase comprises, or is composed, of at least one fatty acid triglyceride, and in particular one edible oil. Commercially available injectable lipid emulsions used for parenteral feeding by infusion, such as Endolipide (Registered Trademark) sold by the Bruneau Company (France) and Intralipide (Registered Trademark) sold by KabiVitrum may be used in particular.

One may also use a lipid phase comprising, or composed of at least one cholesterol ester (e.g., a cholesterol ester derived from a carboxylic acid having 1 to 24 carbon atoms).

One may also use as a lipid phase, lipid vesicles such as liposomes or the like. The composition of such lipid vesicles is known and will not be related here.

Among the drugs that may be incorporated into the lipoproteins according to the method of the invention, the following will be cited: elliptinium, mitoxantrone, ametantrone, methotrexate, doxorubicin, daunorubicin, vincristine, etc., as well as their acylation derivatives with a fatty acid; ketoconazole (or an analog whose acetyl group is replaced by a fatty acid acyl); the acylated derivatives (of fatty acids) of muramyldipeptide; and photoactivatable porphyrin derivatives (Photofrin II).

Examples of active cosmetic substances that can be incorporated into lipoproteins are fat-soluble vitamins (particularly vitamins A and E).

Among the fatty acids whose grafting to the active substance facilitates its incorporation into the lipoproteins, saturated or unsaturated fatty acids having 4 to 24 and in particular 8 to 24 carbon atoms such as, for example, palmitic, stearic, oleic, linolenic, lignoceric, etc. acids, will be cited in particular.

The lipid emulsion can be stabilized with an emulsifier, in particular a phospholipid such as lecithin, which does not degrade protein.

The original lipoprotein may be a native lipoprotein, in particular an LDL.

The native lipoproteins may be separated from the plasma according to known methods and in particular by ultracentrifugation. They may also be isolated from the plasma by filtration through hollow-fiber membranes. LDLs and VLDLs may also be isolated by selective adsorption, for example, on dextran sulfate-cellulose beads (see S. Yokoyama in: "Plasmapheresis:" New trends in therapeutic applications, N.Y. Malchesky and J. W. Smith, Eds., Cleveland, ISAO Press, 231-237 (1983)); and S., Yokoyama et al., Arteriosclerosis, Vol. 5 No. 6, pp. 613-622 (1985)).

A lipoprotein chemically modified to allow it to be recognized by the reticuloendothelial system may also be used as the original lipoprotein. For this purpose, lipoproteins modified according to known methods, for example, acetylated, acetoacetylated, or oxidized LDLs, may be used (see, in particular, J. M. Shaw, op. cit.; Basu et al., Proc. Natl. Acad. Sci. USA 73, 3178-3182 (1976); J. Steinbrechert, Biol. Chem. 262, 3703 (1987)).

The transfer protein used in the process of the invention may be either a known human lipid transfer protein (see above-cited literature) or in general an animal or plant lipid transfer protein. The latter proteins have been described in particular by Basu et al., Biochimica et Biophysica Acta, 959, No. 2, 134-142 (1988) and Grosbois et al., Plant Physiology, 90, No. 4, 1560-1564 (1989).

The transfer protein can also be added in the form of an LPDS plasma fraction, defined as indicated above.

To implement the process of the invention, the lipid emulsion may be prepared by the usual methods, or a ready-made commercial lipid emulsion normally used for parenteral feeding by infusion may be used.

The lipophilic active substance may be added to the emulsion, or vice versa. It is preferable to stir vigorously to ensure good dissolution of the active substance in the lipid phase.

The transfer protein (or the LPDS fraction), which is soluble in water, may then be added with stirring to ensure appropriate homogeneity.

The mixture is then left to incubate for sufficient time for the lipophilic active substance to be incorporated into the lipoprotein.

Once the quantities of lipophilic active substance and lipoprotein have been established, it is easy to experimentally determine the quantity of transfer protein or LPDS necessary to achieve sufficient incorporation of the lipophilic active substance into the lipoprotein.

Likewise, the incubation time necessary to achieve sufficient or maximum incorporation of the lipophilic active substance can be determined in each case by simple routine experiments.

For example, the mixture is left to incubate for 15-20 hours at a temperature of 37° C.

The lipoprotein modified by incorporation of the lipophilic active substance may then be separated by the usual techniques, for example, by density gradient ultracentrifugation or affinity chromatography.

This ensures that any impurity or residual reagent is eliminated, yielding a product essentially exempt of starting products.

Another object of the invention is a lipoprotein, in particular an LDL, modified by incorporation of at least one lipophilic active substance, which can be obtained according to the process indicated above. The lipoprotein thus modified is characterized not only by the presence of the incorporated lipophilic active substance, but also by modified levels of cholesterol (free and esterified) and of triglycerides, relative to the original lipoprotein.

The invention also has as an object a pharmaceutical or cosmetic composition intended for administration or application of at least one lipophilic active substance containing, as the active ingredient, at least one modified lipoprotein as defined above, into which the lipophilic active substance has been incorporated.

The pharmaceutical compositions of the invention are of course used in human or veterinary medicine, in the therapeutic domain corresponding to that of the drug incorporated into the lipoproteins. The dosage (calculated by active substance) is at most equal to and usually less than that of the incorporated drug.

These pharmaceutical compositions are administered parenterally.

The modified lipoproteins according to the invention can also contain lipophilic active substances usable in cosmetic compositions such as fat-soluble vitamins or other lipophilic active principles known to improve the esthetic appearance of the skin. These cosmetic compositions may in particular be in the form of aqueous suspensions or emulsions into which the modified lipoproteins of the invention are incorporated.

The following examples illustrate the invention without, however, limiting it.

EXAMPLE 1

Incorporation of a fatty-chain lipophilic drug into LDLs

A. Equipment

To isolate the LDLs, one begins from blood plasma verified as having negative serology to hepatitis and HIV virus.

The LDLs are isolated by zone ultracentrifugation of the plasma between densities 1.020 and 1.063. They are then dialyzed for 24 hours against an aqueous solution of 0.3 mM EDTA, pH = 8, then sterile-filtered (0.22 μ) and stored in a nitrogen atmosphere.

The emulsion of Endolipide "20%" (Bruneau Company) has the following composition:

Soy oil—20 g
Lecithin—12 g
Glycerol—2 5 g
Water qs.—100 ml

The Endolipide emulsion is washed with an equal volume of normal saline solution (8 g/l NaCl) and then ultracentrifuged for 30 minutes at 30,000 rpm and 10° C. The lipid fraction is then diluted in an equal volume of normal saline.

The purpose of this washing of the Endolipide emulsion is to eliminate the part of the phospholipids (lecithin) which are in fact present in a greater quantity than the sufficient quantity (see E. Granot et al., op. cit.).

The LPDS fraction containing the transfer proteins with densities higher than 1.21 is obtained by ultracentrifugation for 24 hours at 40,000 rpm, 4° C., of a plasma brought to a density of 1.21 g/cm$^3$ by adding KBr (density measured at 20° C.). This LPDS fraction is then dialyzed three times for 12 hours against 10 mM Tris buffer, 140 mM NaCl, 1 mM EDTA, pH 8, and the protein concentration is adjusted to 60 g/l.

The drug incorporated into the LDL is a fatty acid ester of elliptinium (stearate, palmitate, or oleate), a fatty acid ester of ametantrone (monostearate, distearate, monopalmitate, dipalmitate, monooleate, dioleate, monolinolenate, dilinolenate), or a fatty acid ester of mitoxantrone (dilinolenate). These esters were prepared by the method described by Samadi-Baboli, Thesis, University of Toulouse III, 1989.

B. Method

One mg of drug is dissolved in the minimum quantity of an organic solvent (chloroform) then the solvent is evaporated under reduced pressure.

Two hundred μl of washed Endolipide are then added. The tube is shaken vigorously, swirling for 1 minute to dissolve the drug in the lipid phase. The LDLs are then added in a quantity containing 1 mg of proteins, assayed by the method of Lowry modified by Peterson (see Lowry et al., J. Biol. Chem. 193, 265–275 (1951)) and 5 ml of LPDS. After stirring, the mixture is incubated for 18 hours at 37° C.

The LDLs are then separated by ultracentrifugation according to a KBr density gradient (centrifugation for 24 hours at 4° C. and 40,000 rpm).

The LDLs modified by affinity chromatography can also be isolated by known methods.

The modified LDLs are then dialyzed against an NaCl solution, 140 mM, pH 8, then filtered under sterile conditions (0.22 μm) and stored under nitrogen.

Similar modified LDLs can be obtained by replacing the Endolipide by a microemulsion obtained as follows: 2 mg of drug, 1 mg of cholesterol stearate, and 2 mg of phospholipids are dissolved in 1 ml of chloroform. The mixture is stirred until it is thoroughly homogenized, after which the solvent is evaporated. The residue is treated with 200 μl of isopropanol and the solution obtained is injected into 3 ml of buffer (0.2 M phosphate, 0.15 M NaCl pH 7.4) with vigorous stirring, swirling for at least 1 minute. The final step is gelfiltration (G 26) in the phosphate buffer.

C. Analyses

The following tests were made on the modified and native LDLs:

proteins: according to Lowry's technique modified by Peterson;

lipids (free cholesterol, esterified cholesterol, triglycerides, phospholipids): tested by enzyme methods (see J. C. Fruchart et al., Pharmacol. Biol., 24, 227–229, 1980; J. Ziegenhorn et al., Clin. Chem., 26, 973–979 (1980); M. Takayama et al., Clinica Chim. Acta, 79, 93–98 (1977));

drugs (on the modified LDLs): the ametantrone esters were tested after precipitation of apolipoprotein B with isopropanol. For this purpose, 100 μl of LDL are added to 100 μl of isopropanol and stirred for 1 minute then left to stand overnight at 10° C. with stirring. The mixture is then centrifuged for 30 minutes at 300 rpm. The supernatant is removed and evaporated. The residue is treated with 1 ml of chloroform. The optical density is read off at a wavelength of 614 nm and compared to a reference range of the drug.

The elliptinium esters are tested by HPLC according to the technique described by Samadi-Baboli (thesis cited above).

D. Pharmacologic Studies

The metabolism of the modified LDLs was studied in rabbits by comparing the kinetics of plasma clearance of native LDLs and that of modified LDLs injected into the bloodstream.

The cytotoxic effects of the LDLs modified by incorporation of elliptinium oleate were studied on L 1210 cells in the presence of increasing drug concentrations. Cell growth was measured after 48 hours' incubation by counting with a Coulter counter.

The results obtained are summarized below.

1. Proteins

The apolipoprotein B from the modified proteins retains its antigenic properties to anti-LDL antibodies.

2. Lipids

The lipid compositions are given as a function of protein (apo B) concentration. The apo B content of the native LDLs is one apo B molecule per particle of LDL. This content is unchanged after modification according to the method of the invention.

The total cholesterol content of the LDLs modified according to the method indicated above is 13% instead of 39% for the original native LDLs.

The triglyceride content is increased (41% in modified LDLs compared to 8% in native LDLs).

The phospholipid content is practically unchanged (18% for modified LDLs compared to 22% for the original native LDLs).

3. Electrophoretic Mobility

The mobility of the modified LDLs is identical to that of the original LDLs.

4. Recognition of Apoprotein B and E Receptor

Competition methods were used to check that the LDLs modified by incorporation of mitoxantrone dilinolenate bonded to the apo B and E receptors of HeLa cells, just like native LDLs.

Likewise, with LDLs modified by incorporation of elliptinium oleate, there is no significant difference in the binding, internalization, or degradation between native LDLs and modified LDLs (tested on human skin fibroblasts).

5. Quantities of Drug Incorporated into LDLs

The following uptakes were obtained:

a. Elliptinium stearate: 37 μg per mg of protein
palmitate: 58 μg per mg of protein
oleate: 83 μg per mg of protein b. Ametantrone not esterified: 1 molecule/particle of LDL
monostearate: 1 molecule/particle
distearate: 1 molecule/particle
monopalmitate: 2 molecules/particle
dipalmitate: 2 molecules/particle
monooleate: 2 molecules/particle
dioleate: 2 molecules/particle
monolinolenate: 80 molecules/particle
dilinolenate: 90 molecules/particle c. Mitoxantrone not esterified: 1 molecule/particle
dilinolenate: 22 molecules/particle 6. Metabolism This study showed that the decline in plasma concentration of modified LDLs (mitoxantrone dilinolenateLDL) labeled with iodine 131 is close to the curve of the plasma decline of native LDLs labeled with iodine 125. This study shows that LDLs modified by incorporation of drug are not captured by the reticuloendothelial system.

7. Cytotoxicity

This study was performed on L1210 cells (see Samadi-Baboli thesis cited above).

The addition of increasing doses of modified LDLs containing elliptinium oleate showed that the modified LDLs are distinctly more toxic than elliptinium oleate added alone at the same concentration.

This cytotoxicity depends on the receptor for the apolipoproteins, since an excess of native LDLs added to a constant concentration of modified LDLs restores cell growth, while an excess of methylated LDLs, incapable of binding to the receptor, has no effect.

The lipoproteins according to the invention can be formulated with any pharmaceutically or cosmetically acceptable excipient to create classical galenical or pharmaceutical forms such as lotions, solutions, etc.

The lipoproteins can be administered topically or parenterally and in the latter case can be formulated in an injectable buffer preferably at the rate of 0 05 to 1% and more particularly, from 0.1 to 0.4%.

For example, a phosphate or carbonate buffer which may contain an antioxidant such as vitamin E or probucol in a sufficient quantity to prevent oxidation, can be used.

FORMULATION EXAMPLES a. Elliptinium oleate
Modified LDLs of Example 1—0.5%
Phosphate buffer 10 raM, pH 7.4 with
20 mM vitamin E, qs—100% b. Ametantrone monolinolenate
Modified LDLs of Example 1—0.2%
Phosphate buffer 10 mM, pH 7.4 with
20 mM vitamin E, qs—100% c. Ametantrone dilinolenate
Modified LDLs of Example 1—0 2%
Phosphate buffer 10 mM, pH 7.4 with
20 mM vitamin E, qs—100%

What is claimed is:

1. A method of preparing a lipoprotein modified by incorporation of at least one lipophilic active substance other than a triglyceride or a cholesterol ester, comprising a) incorporating said at least one active substance into an emulsion of a lipid phase in a continuous aqueous phase; b) adding to the emulsion, with stirring, a starting lipoprotein and at least one lipid transfer protein to form a mixture; c) allowing the mixture to incubate; and d) isolating the lipoprotein into which the active substance is incorporated.

2. Method according to claim 1, wherein the lipid phase comprises at least one fatty acid triglyceride.

3. Method according to claim 1, wherein said lipid phase comprises at least one cholesterol ester.

4. Method according to claim 1, wherein said lipid phase comprises lipid vesicles.

5. Method according to claim 4, wherein said at least one lipid transfer protein is added in the form of a lipoprotein-deficient serum plasma fraction.

6. Method according to claim 4, wherein the lipid vesicles are liposomes.

7. Method according to claim 1, wherein said emulsion is stabilized with the aid of an emulsifier.

8. Method according to claim 7, wherein said emulsifier is a phospholipid.

9. Method according to claim 8, wherein said emulsifier is lecithin.

10. Method according to claim 1, wherein said starting lipoprotein is a native lipoprotein.

11. Method according to claim 10, wherein said native lipoprotein is an LDL.

12. Method according to claim 1, wherein said starting lipoprotein is a chemically modified lipoprotein.

13. Method according to claim 2, wherein said starting lipoprotein is an LDL, modified chemically to allow it to be recognized by the reticuloendothelial system.

14. Method according to claim 13, wherein said starting LDL is an acetylated, acetoacetylated, lactosylated, or oxidized LDL.

15. Method according to claim 1, wherein said starting lipoprotein is a human lipoprotein.

16. Method according to claim 1, wherein said at least one lipid transfer protein is an animal or plant lipoprotein.

17. Method according to claim 1, wherein said at least one active substance is an antitumoral substance.

18. Method according to claim 1, wherein the at least one lipophilic active substance is a hydrophilic drug, chemically modified to become more lipophilic.

19. Method according to claim 1, wherein said at least one active substance is an antiproliferative substance.

20. Method according to claim 1, wherein said at least one active substance is an antiparasitic substance.

21. Method according to claim 1, wherein said at least one active substance is an antifungal substance.

22. Method according to claim 1, wherein said at least one active substance is an antiviral substance.

23. Method according to claim 1, wherein said at least one active substance is an antiviral substance.

24. Method according to claim 1, wherein said at least one active substance is at least one fat-soluble vitamin.

* * * * *